United States Patent
Tzonev et al.

(10) Patent No.: US 6,258,088 B1
(45) Date of Patent: Jul. 10, 2001

(54) SWITCH FOR ELECTROSURGICAL TOOL FOR PERFORMING CUTTING, COAGULATION, AND SUCTIONING

(75) Inventors: Nikolay Nikolov Tzonev; Lyndon Charles Crossman, both of Victoria; Robert H. Brown, Abbotsford, all of (CA)

(73) Assignee: Robert H. Brown, M.D., Inc. (CA)

( * ) Notice: Subject to any disclaimer, the term of this patent is extended or adjusted under 35 U.S.C. 154(b) by 0 days.

(21) Appl. No.: 09/373,102

(22) Filed: Aug. 12, 1999

(51) Int. Cl.$^7$ .................................................... A61B 18/14
(52) U.S. Cl. ................... 606/42; 606/45; 606/49; 604/35; 200/293.1
(58) Field of Search ................... 606/42, 45, 49; 604/35; 200/293.1

(56) References Cited

U.S. PATENT DOCUMENTS

| | | |
|---|---|---|
| 2,275,167 | 3/1942 | Bierman . |
| 3,494,363 | 2/1970 | Jackson . |
| 3,801,766 | 4/1974 | Morrison, Jr. . |
| 4,872,454 | 10/1989 | DeOliveira et al. . |
| 4,911,159 | 3/1990 | Johnson et al. . |
| 5,071,418 | 12/1991 | Rosenbaum . |
| 5,160,334 | 11/1992 | Billings et al. . |
| 5,195,959 * | 3/1993 | Smith ........................ 604/34 |
| 5,318,565 | 6/1994 | Kuriloff et al. . |
| 5,468,240 | 11/1995 | Gentelia et al. . |
| 5,496,314 * | 3/1996 | Eggers ........................ 606/41 |
| 5,620,441 | 4/1997 | Greff et al. . |
| 5,674,219 | 10/1997 | Monson et al. . |
| 5,800,431 | 9/1998 | Brown . |
| 5,830,214 * | 11/1998 | Flom et al. ..................... 606/41 |
| 5,951,548 * | 9/1999 | DeSisto et al. ................. 606/42 |

* cited by examiner

*Primary Examiner*—Lee Cohen
(74) *Attorney, Agent, or Firm*—Townsend and Townsend and Crew LLP

(57) ABSTRACT

A switch for use with an electrosurgical tool having a heatable tip connectable to a power source and a suction passage connectable to a suction source. The switch comprises a main body having a suction passage extending therethrough connectable to the suction passage of the tool. A cavity in the main body intersects the suction passage and is adapted to slidably receive a mounting post to permit slidable movement of the main body over the mounting post. The mounting post has an end protruding from the main body that is pivotally connectable to the tool. An opening extends through the mounting post that is alignable with the suction passage. In operation, the main body of the switch is manually movable between a default position in which the suction passage and the opening are misaligned to block suction and an operating position in which the suction passage and opening are aligned to permit suction. In the operating position, the main body pivots with the mounting post to permit electrical connection of the heatable tip to the power source to perform cutting or coagulating.

10 Claims, 3 Drawing Sheets

SWITCH FOR ELECTROSURGICAL TOOL FOR PERFORMING CUTTING, COAGULATION, AND SUCTIONING

FIELD OF THE INVENTION

This invention relates to a medical device, and more specifically, to a switch and an electrosurgical tool incorporating the switch for performing cutting and coagulation of tissue at an operation site, and simultaneous suctioning of generated smoke.

BACKGROUND OF THE INVENTION

In surgery performed on patients, surgeons generally employ electrosurgical tools to cut tissue and to coagulate bleeding blood vessels in a process known as cautery. An example of a prior art electrosurgical tools is found in U.S. Pat. No. 4,872,454 to DeOliveira et al.

In order to keep the operation site visible, continuous suction devices are used to suction away blood and other debris before they accumulate and to remove smoke that is generated by the electrical cautery process. This suction is vital so that the surgeon's view of the operation site remains unobscured and the operation can proceed safely.

Previously, separate tools were necessary to perform the cautery process and suctioning. If a surgeon uses both tools simultaneously, both hands are occupied which tends to increase the difficulty of the procedure. Use of a separate suctioning device also makes precise positioning of the electrosurgical tool more difficult. To effectively use both devices simultaneously, it is often necessary for an assistant to operate the suction device as the surgeon operates the electrosurgical tool.

To address the foregoing shortcomings of using separate electrosurgical tools and suctioning tools, various combined tools have been developed as disclosed in the following patents:

U.S. Pat. No. 3,494,363 to Jackson
U.S. Pat. No. 4,911,159 to Johnson et al.
U.S. Pat. No. 5,071,418 to Rosenbaum
U.S. Pat. No. 5,318,565 to Kuriloff et al.
U.S. Pat. No. 5,468,240 to Gentelia et al.

The tools disclosed in the above patents use different control schemes for controlling suction while simultaneously operating the cutting and coagulation parts of the tool. In several of the patents, suction must operate continuously as the suction force is also used to control whether the cutting or coagulation function of the tool is selected. This is achieved by the covering or uncovering of various open ports on the body of the tool by the fingers of the user to select a cutting or coagulation mode.

U.S. Pat. No. 5,800,431 to Brown is a prior art tool developed by a co-inventor of the tool of the present invention. The Brown tool has a manually actuatable switch that starts operation of the suction action. When the cutting or coagulation functions are not being used, the suction action is automatically stopped.

SUMMARY OF THE INVENTION

The present invention provides an improved switch and electrosurgical tool that combines suction, cutting and coagulation functions. The switch is easy to manipulate to control selection of one of the cutting and coagulation functions while automatically providing suction. The switch provides reliable operation with a minimum of moving parts.

Accordingly, the present invention provides a switch for use with an electrosurgical tool having a heatable tip connectable to a power source and a suction passage connectable to a suction source, the switch comprising:

a main body having a suction passage extending therethrough connectable to the suction passage of the tool;

a cavity in the main body intersecting the suction passage of the main body;

a mounting post adapted to be slidably received in the cavity to permit slidable movement of the main body over the mounting post, the mounting post having an end protruding from the main body that is pivotally connectable to the tool; and an opening extending through the mounting post alignable with the suction passage;

whereby the main body of the switch is manually movable between a default position in which the suction passage and the opening are misaligned to block suction and an operating position in which the suction passage and opening are aligned to permit suction, the main body pivoting with the mounting post in the operating position to permit electrical connection of the heatable tip to the power source to perform cutting or coagulating.

In a further aspect, the present invention provides an electrosurgical tool for use with a power source and a suction source comprising:

a handle for gripping by the user;

an electrically heatable tip extending from the handle and being electrically connectable to the power source;

a suction passage formed in the handle connectable to the suction source; and a manually actuatable switch comprising a main body having a suction passage extending therethrough connectable to the suction passage of the tool;

a cavity in the main body intersecting the suction passage of the main body;

a mounting post adapted to be slidably received in the cavity to permit movement of the main body over the mounting post, the mounting post having an end protruding from the main body that is pivotally connectable to the handle; and an opening extending through the mounting post alignable with the suction passage;

whereby the main body of the switch is manually movable between a default position in which the suction passage and the opening are misaligned to block suction and an operating position in which the suction passage and opening are aligned to permit suction, the main body pivoting with the mounting post in the operating position to electrically connect the heatable tip to the power source to perform cutting or coagulating.

Operation of the suction tends to be noisy and employing automatic suction only when the tool is performing cutting or coagulation diminishes irritating and unnecessary noise in the operation room.

BRIEF DESCRIPTION OF THE DRAWINGS

Aspects of the present invention are illustrated, merely by way of example, in the accompanying drawings in which.

DESCRIPTION OF THE PREFERRED EMBODIMENT

Figure 1:
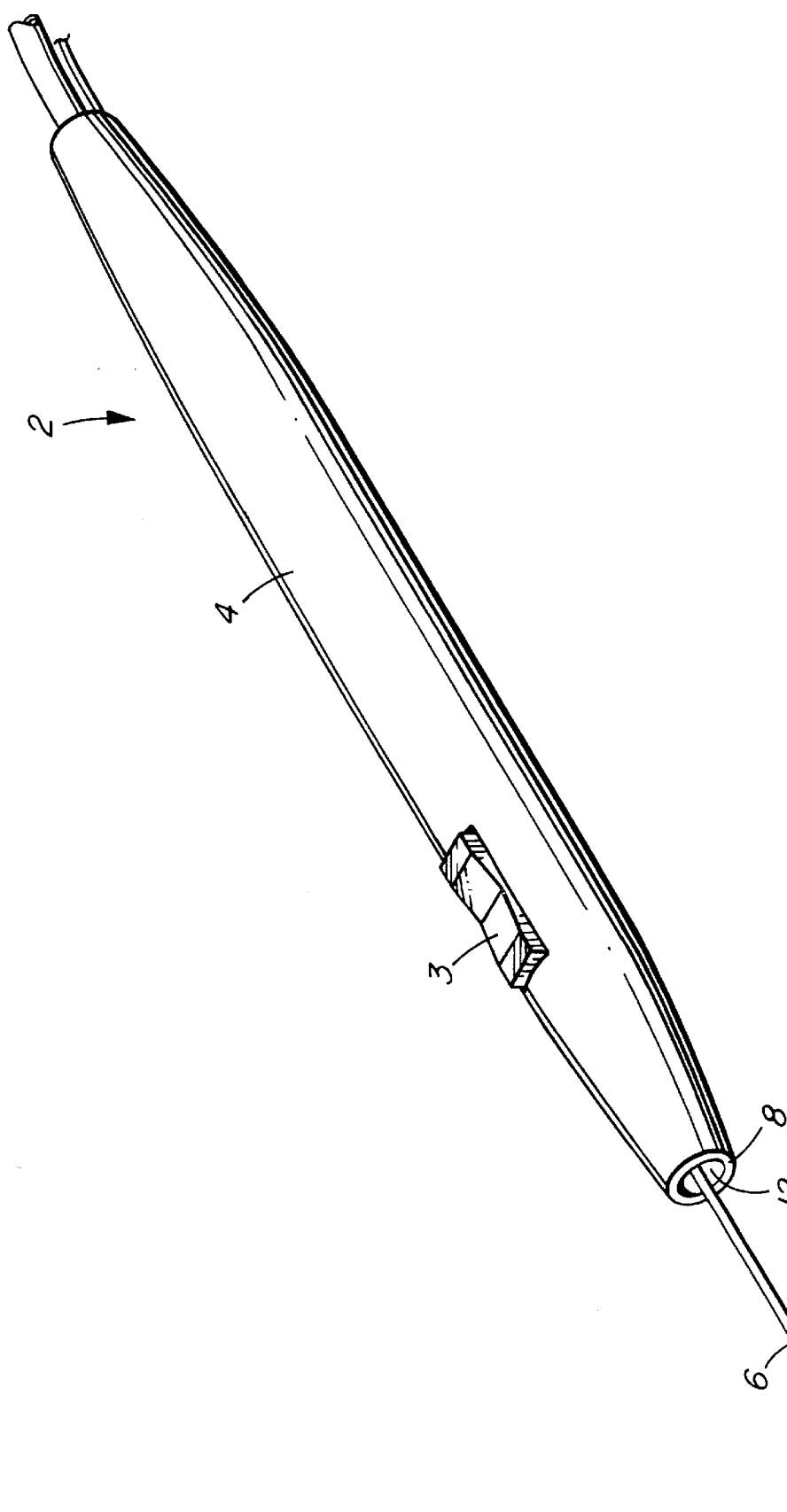
FIG. 1 is a perspective view of an electrosurgical tool incorporating the switch of the present invention.
Figure 2:
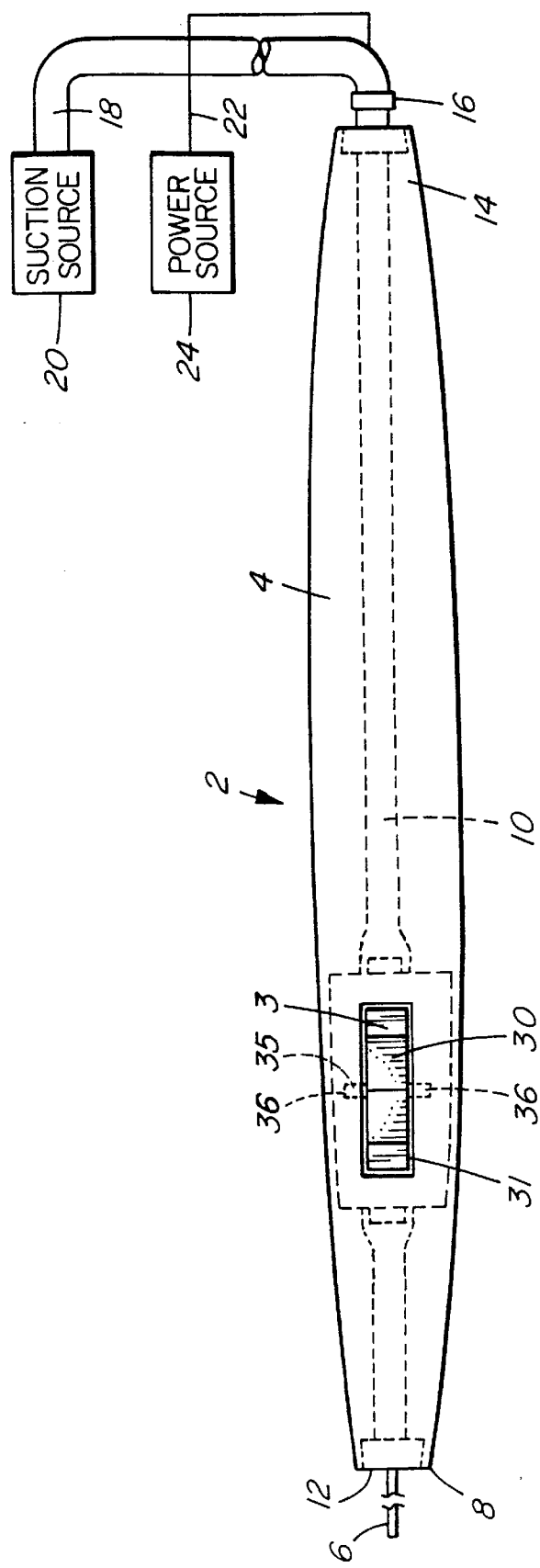
FIG. 2 is a plan view of the electrosurgical tool of FIG. 1.

Referring to FIGS. 1 and 2, there is shown an electrosurgical tool 2 incorporating the switch 3 o the present invention. Tool 2 comprising a moulded handle 4 for comfortable gripping by the user having an electrically heatable tip 6 extending from the front end 8 of the handle. Handle 4 is formed with an internal passage 10 that extends from opening or suction port 12 at front end 8 to a connector 16 at the rear 14 of the handle.

As shown schematically in FIGS. 1 and 2, connector 16 is connectable via tubing 18 to a conventional medical suction source 20. Likewise, electrically heatable tip 6 is connected via wiring 22 to a conventional power source 24 that provides current for heating tip 6 to permit cutting or coagulation. Power source 24 is preferably a conventional uni-polar cautery machine. As will be understood by a person skilled in the art, the cautery machine supplies current continuously to tip 6 to allow the attached electrosurgical tool to operate in cutting mode. Tip 6 heats the tissue so that the cells are desiccated very quickly and literally explode to create an incision. In the coagulation mode of the tool, current is delivered in short pulses with pauses between pulses. This results in the tip heating the tissue more slowly resulting in relatively slow dehydration of the cells without exploding.

Heatable tip 6 comprises a rigid metal probe mounted to handle 4 to extend from suction port 12. By appropriate heating of tip 6 as will be discussed further, tip 6 can be used as a cutting instrument or as a tool to coagulate blood vessels.

Figure 3:
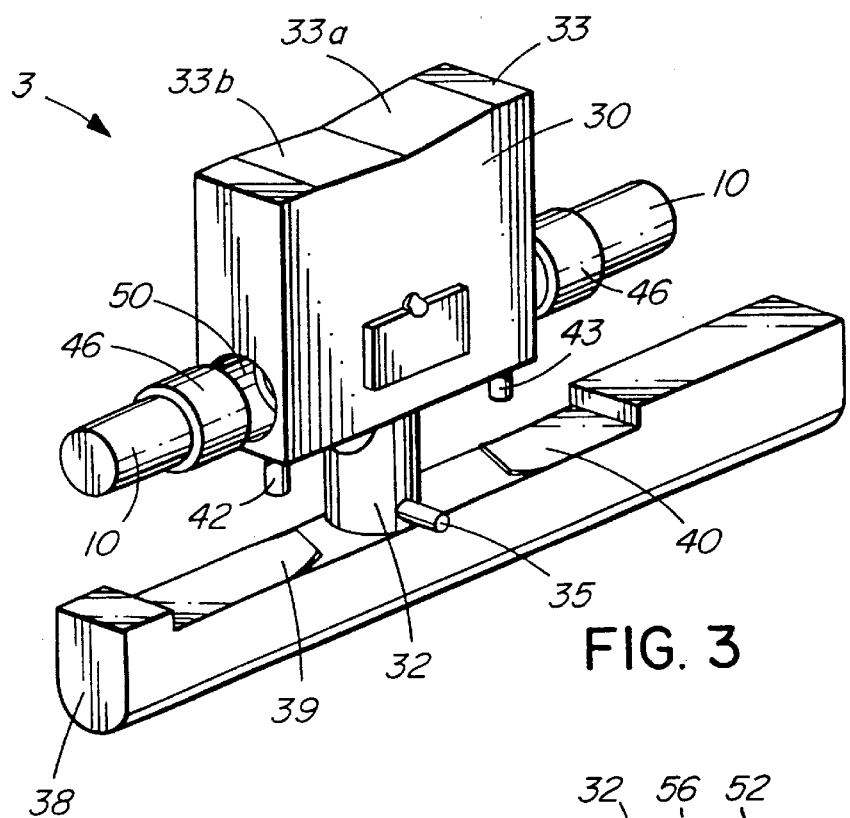
FIG. 3 is a detail view of a preferred embodiment of the switch of the present invention.

FIG. 3 is a detail view of the switch 3 incorporated within electrosurgical tool 2. Switch 3 comprises a main body 30 that is slidably mounted on a mounting post 32. Mounting post 32 is pivotally connected to tool 2 by pin 35. As best shown in FIG. 2, main body 30 fits within a generally rectangular cavity 31 formed within the upper surface of tool handle 4. The upper surface 33 of main body 30 protrudes from the handle to be manipulated by the user. Pin 35 extends through a hole in the base of post 32 and has ends 36 that are retained in holes in tool handle 4 to pivotally interconnect the switch with the tool.

Figure 4A:
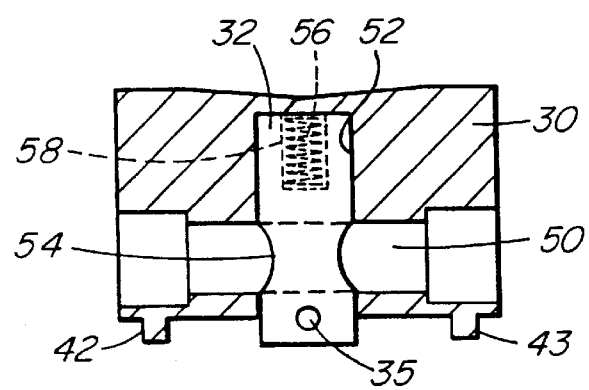
FIG. 4a is a sectional view through the main body of the switch showing main body in the operating position of the switch.
Figure 4B:
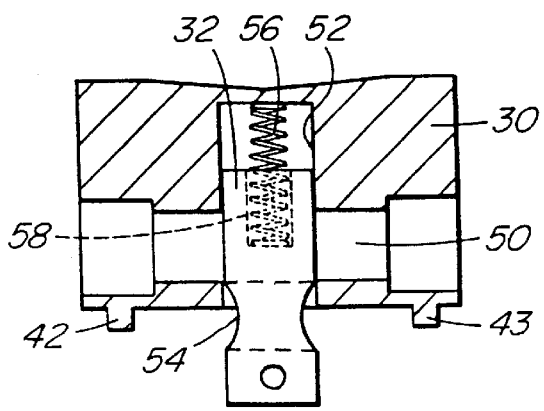
FIG. 4b is a sectional view through the main body of the switch showing the main body in the raised default position of the switch.

Referring to FIGS. 3, 4a and 4b, main body 30 of switch 3 is formed with a suction passage 50 extending through the lower region of the body. Ends 46 of suction passage 10 of tool 2 are insertable into passage 50 to create a continuous passage through the tool to communicate suction port 12 with suction source 20. Main body 30 also includes a central cavity 52 that intersects suction passage 30. Mounting post 32 is slidably received in cavity 52 to interconnect main body 30 and mounting post 32 such that the main body is movable up and down along the mounting post. The mounting post is dimensioned such that the base and pin 35 always protrude from the lower side of main body 30.

Figure 5:
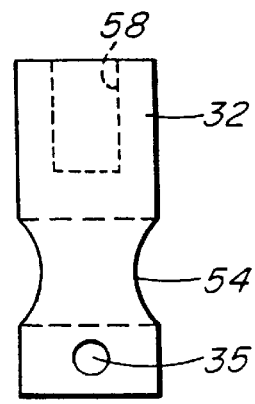
FIG. 5 is a detail view of the mounting post of the switch.

As best shown in FIG. 5, which is a detail view of mounting post 32, there is an opening 54 extending through mounting post 32. Opening 54 is alignable with suction passage 50 by movement of main body 30 on mounting post 32. FIG. 4a shows main body 30 positioned on mounting post 32 such that opening 54 is aligned with passage 50. This is the operating position of the switch which allows suction to be generated at suction port 12 of the tool. To position the switch in the arrangement shown in FIG. 4a, the user must press on switch 3. By default, main body 30 and mounting post are positioned as shown in FIG. 4b with opening 54 and passage 50 misaligned. This causes mounting post 32 to block passage 50 so that suction is not generated at suction port 12 of electrosurgical tool 2.

Preferably, biasing means in the form of coil spring 56 are positioned within cavity 52 between main body 30 and mounting post 32 to bias the parts into the default position of FIG. 4b. Mounting post 32 is formed with an internal cavity 58 to retain spring 56.

While main body 30 of switch 3 is depressed by the user to the operating position of FIG. 4a, the main body can be pivoted with mounting post 32 about pin 35 to permit electrical connection of heatable tip 6 to power source 24 to perform cutting or coagulating. As best shown in FIG. 3, switch 3 is mounted in electrosurgical tool 2 over a conventional electrical contact member 38 3. Electrical contacts 39 and 40 are formed at each end of contact member 38 to define an electrical circuit which is normally open when main body 30 is in the default raised position to disconnect the tip from the power source. Main body 30, when depressed to generate suction, is used to manipulate contacts 39 or 40 to selectively deliver power to the tip to provide cutting or coagulation. When closed, one contact will electrically connect tip 6 to power source 24 for heating in a manner that produces cutting of tissue while the other contact will connect tip 6 to power source 24 for heating in a manner that causes coagulation of tissue.

To manipulate contacts 39 and 40, main body 30 is formed with downwardly depending projections 42 and 43 at opposite sides of the body that act to engage and depress electrical contact 39 and 40, respectively, when main body 30 is pivoted about pin 35 rearwardly or forwardly with respect to tool 2. This pivoting is achieved by the user pressing on one end or the other of exposed upper surface 33 of main body 30. Preferably, upper surface 33 is formed with angled surfaces 33a and 33b to provide a comfortable location for a user's finger to rest when simultaneously depressing and pivoting switch 3 to create suction at the tool tip and to select the desired mode of heating of tip 6. Necessarily, suction passage 10 through electrosurgical tool 2 includes some slack to accommodate pivoting of main body 30 to which suction passage 10 is connected.

Contacts 39 and 40 are illustrated in FIG. 3 as being resilient flaps of electrically conductive material that are pressed by protrusions 42 or 43 to complete a circuit. It will be readily apparent to a person skilled in the art that contacts 39 and 40 can be formed from any suitable selector switches that are urged from an open state into a closed state by engagement with protrusions 42 or 43.

Furthermore, it will be readily apparent that the direction that main body 30 is pivoted to select for cutting or coagulation is dependent on whether current for cutting or current for coagulation is being delivered through the contact 39 or contact 40. Main body 30 is preferably marked with an appropriate designation such as CUT and COAG on the inclined surface 33a or 33b of the switch that must be depressed to achieve the indicated operation.

The switch of the present invention operates to generate suction first by aligning opening 54 with passage 50 whereupon the desired heating of tip 6 is selected by pivoting of main body 30 of the switch. This arrangement ensures that the operation site is effectively cleared of smoke generated during cutting or coagulation. By placing suction port 12 directly at the front of handle 4 adjacent tip 6, any smoke generated by tip 6 is immediately suctioned away to keep the surgeon's field of view clear.

Although the present invention has been described in some detail by way of example for purposes of clarity and understanding, it will be apparent that certain changes and modifications may be practiced within the scope of the appended claims.

What is claimed is:

1. A switch for use with an electrosurgical tool having a heatable tip connectable to a power source and a first suction passage connectable to a suction source, the switch comprising:

a main body having a second suction passage extending therethrough connectable to the first suction passage of the tool;

a cavity in the main body intersecting the second suction passage of the main body;

a mounting post adapted to be slidably received in the cavity to permit slidable movement of the main body over the mounting post, the mounting post having an end protruding from the main body that is pivotally connectable to the tool; and an opening extending through the mounting post alignable with the second suction passage;

whereby the main body of the switch is manually movable between a default position in which the second suction passage and the opening are misaligned to block suction and an operating position in which the second suction passage and opening are aligned to permit suction, the main body pivoting with the mounting post in the operating position to permit electrical connection of the heatable tip to the power source to perform cutting or coagulating.

2. A switch as claimed in claim 1 including a spring in the cavity to bias the main body and the mounting post into the default position.

3. A switch as claimed in claim 2 in which the default position is a raised position of the main body on the mounting post and the operating position is a depressed position of the main body on the mounting post.

4. A switch as claimed in claim 1 including projections formed on the main body to engage electrical contacts in the tool to electrically connect the heatable tip to the power source.

5. A switch as claimed in claim 4 in which the main body is pivotable rearwardly or forwardly with respect to the tool to engage either first electrical contacts that connect the heatable tip to the power source to heat the tip to perform cutting or second electrical contacts that connect the heatable tip to the power source to heat the tip to perform coagulation.

6. An electrosurgical tool for use with a power source and a suction source comprising;

a handle for gripping by the user;

an electrically heatable tip extending from the handle and being electrically connectable to the power source;

a first suction passage formed in the handle connectable to the suction source; and a manually actuatable switch comprising a main body having a second suction passage extending therethrough connected to the first suction passage of the tool;

a cavity in the main body intersecting the second suction passage of the main body;

a mounting post slidably received in the cavity to permit movement of the main body over the mounting post, the mounting post having an end protruding from the main body that is pivotally connected to the handle; and an opening extending through the mounting post alignable with the second suction passage;

whereby the main body of the switch is manually movable between a default position in which the second suction passage and the opening are misaligned to block suction and an operating position in which the second suction passage and opening are aligned to permit suction, the main body pivoting with the mounting post in the operating position to electrically connect the heatable tip to the power source to perform cutting or coagulating.

7. An electrosurgical tool as claimed in claim 6 including an electrical circuit operable by the main body of the switch to electrically connect the heatable tip to the power source.

8. An electrosurgical tool as claimed in claim 7 in which the electrical circuit is open when the main body is in the default position to disconnect the tip from the power source and which is selectively closed when the main body is moved to the operating position and pivoted rearwardly or forwardly to deliver power to the tip to provide cutting or coagulation.

9. An electrosurgical tool as claimed in claim 8 in which the electrical circuit includes contacts that are urged from an open state into a closed state by protrusions on the main body of the switch.

10. An electrosurgical tool as claimed in claim 6 in which the electrically heatable tip comprises a rigid metal probe extending from the handle.

* * * * *